(12) United States Patent
Da Silva et al.

(10) Patent No.: US 7,940,038 B2
(45) Date of Patent: May 10, 2011

(54) GRID SENSOR FOR THE TWO-DIMENSIONAL MEASUREMENT OF DIFFERENT COMPONENTS IN THE CROSS SECTION OF A MULTIPHASE FLOW

(75) Inventors: Marco Jose Da Silva, Dresden (DE); Eckhard Schleicher, Dresden (DE); Uwe Hampel, Dresden (DE); Horst-Michael Prasser, Dättwil (CH)

(73) Assignee: Helmholtz-Zentrum Dresden-Rossendorf e.V., Dresden (DE)

( * ) Notice: Subject to any disclaimer, the term of this patent is extended or adjusted under 35 U.S.C. 154(b) by 373 days.

(21) Appl. No.: 12/297,954

(22) PCT Filed: Apr. 18, 2007

(86) PCT No.: PCT/DE2007/000653
§ 371 (c)(1),
(2), (4) Date: Oct. 21, 2008

(87) PCT Pub. No.: WO2007/121708
PCT Pub. Date: Nov. 1, 2007

(65) Prior Publication Data
US 2009/0102450 A1 Apr. 23, 2009

(30) Foreign Application Priority Data
Apr. 21, 2006 (DE) .................... 10 2006 019 178

(51) Int. Cl.
*G01R 31/02* (2006.01)
*G01R 27/26* (2006.01)
*G01R 27/08* (2006.01)

(52) U.S. Cl. .......... 324/72; 324/663; 324/686; 324/701; 324/713; 324/715; 324/724

(58) Field of Classification Search .............. 324/72, 324/658, 663, 664, 686, 689–691, 693–696, 324/701, 713, 715, 722, 724
See application file for complete search history.

(56) References Cited

U.S. PATENT DOCUMENTS

| 4,644,263 | A | * | 2/1987 | Johnson ................... 324/717 |
| 4,658,208 | A | * | 4/1987 | Lee et al. ................. 324/686 |
| 5,164,675 | A | * | 11/1992 | Howe et al. .............. 324/663 |
| 5,210,499 | A | * | 5/1993 | Walsh ...................... 324/724 |
| 5,287,752 | A | * | 2/1994 | Den Boer ................. 73/861.04 |
| 6,314,373 | B1 | * | 11/2001 | Prasser et al. ............ 324/693 |

* cited by examiner

*Primary Examiner* — Timothy J Dole
(74) *Attorney, Agent, or Firm* — Laurence A. Greenberg; Werner H. Stemer; Ralph E. Locher

(57) ABSTRACT

Disclosed is an arrangement for quickly measuring the phase distribution or the component distribution in a flow cross section for substance mixtures also of a non-conducting type by measuring the complex electrical admittance. Said arrangement essentially features the following: at least one sine wave generator (5) which is mounted upstream from the transmitter electrodes (3a) of the excitation level and applies an alternating voltage to the transmitter electrodes (3a); current-to-voltage converters (7) which are mounted downstream from the receiver electrodes (3b), amplify the alternating current that flows from at least one excitation electrode (3a) through the medium to the receiver electrodes (3b), and convert said alternating current into a voltage signal; filter groups (10, 11, 16) and vector voltmeters (8) which are mounted downstream from the current-to-voltage converters (7) and allow the complex signal ratio $U_a/U_e$ to be metrologically detected.

6 Claims, 4 Drawing Sheets

Figure 1:
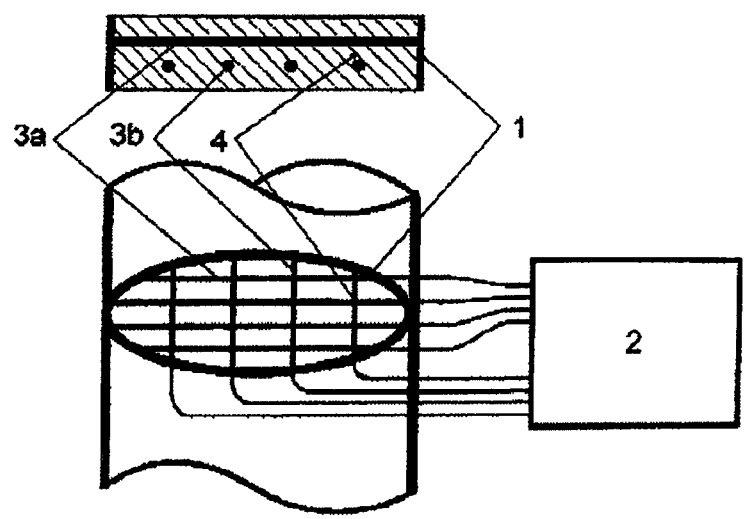

GRID SENSOR FOR THE TWO-DIMENSIONAL MEASUREMENT OF DIFFERENT COMPONENTS IN THE CROSS SECTION OF A MULTIPHASE FLOW

The invention relates to a measuring arrangement for investigating multiphase or multicomponent flows. Typical areas of use are the analysis of multiphase flows in chemical process engineering and oil production and processing.

U.S. Pat. Nos. 4,644,263, 5,210,499 and DE 19 649 011 describe arrangements which are in the form of grids and can be used to investigate two-phase media with the aid of a two-dimensional conductivity measurement. In these arrangements, DC voltage or bipolar square-wave voltage signals are successively applied to the electrodes in the form of wires on one electrode level and a current signal is simultaneously detected at the electrodes on the other electrode level. As a result, these arrangements are able to determine the conductivity at the crossover points of the electrodes. For a two-phase flow with precisely one conductive phase (for example a gas/water mixture), it is therefore possible to determine the phase distribution in the flow cross section by recording the conductivity distribution. Phase discrimination for phases or components of a flow which have similarly good or poor conductivity is not directly possible with these arrangements.

U.S. Pat. No. 5,287,752 describes an arrangement for investigating a multiphase flow, in which a pair of immovable parallel plates is fitted inside a pipeline. The plates have a plurality of segments which are used as capacitive sensors. Said document describes that sinusoidal voltage excitation can be used to investigate a multiphase mixture by means of complex admittance measurement.

The abovementioned arrangements for measuring the conductivity have a considerable disadvantage. These sensors cannot be used to distinguish non-conductive phases or components of a flow. In contrast, the arrangement disclosed in U.S. Pat. No. 5,287,752 cannot be used to visualize the phase distribution in a pipe cross section since the penetration of a sensor plate greatly influences the flow and allows only the detection of the phase distribution on the surface of the sensor arrangement.

The object of the present invention is to specify an arrangement for quickly measuring the phase or component distribution in a flow cross section, for non-conductive mixtures of substances as well, on the basis of a measurement of the complex electrical admittance.

The object is achieved by means of the features of claim 1. Refinements of the invention are stated in the subclaims.

The novelty of the invention is the possibility of quick two-dimensional measurement of both the electrical admittance (or conductivity) and the electrical capacitance (or permittivity) of the mixture of substances.

This arrangement and a connected electronic data processing process make it possible to detect, represent and evaluate phase and/or component distributions in a flow cross section, for example inside a pipeline, of a reactor vessel or another flow-carrying vessel with a very high temporal resolution.

The invention is explained in more detail below using an exemplary embodiment. Some variants are also described in the process.

The figures illustrated are concomitantly described in the description of the exemplary embodiment.

The arrangement according to FIG. 1 comprises a grid sensor (1) having at least two electrode levels, which are at a short distance from one another, and associated measurement electronics (2). The grid sensor has two levels of electrodes in the form of wires, the transmitting electrodes (3a) and the receiver electrodes (3b), which are arranged parallel to one another and at a short distance from one another inside each level. The electrodes on different levels are oriented approximately perpendicular to one another. The complex electrical admittance of the medium between the transmitting electrodes (3a) and the receiver electrodes (3b) is measured at each individual crossover point (4) of the electrode grid.

In order to measure the complex electrical admittance (FIG. 2) of the medium at the individual crossover point (4), an AC voltage is applied to the associated transmitting electrode (3a) using a sine-wave generator (5). At the same time, the alternating current flowing through the investigation medium at the crossover point is converted, at the receiver electrode (3b), into an AC voltage signal using a current-voltage converter (7) which is connected to the electrode. This AC voltage signal is then detected and evaluated using a vector voltmeter (8) whose reference signal is branched off from the excitation signal. The vector voltmeter (8) provides the real and imaginary parts of the voltage signal, or, equivalently, its magnitude and phase, relative to the excitation signal of the sine-wave generator (5). In order to arrive at a two-dimensional image of the phase or component distribution at the grid level, the complex admittances of the grid crossover points (4) must be measured very quickly at the same time or in succession. This can be carried out with the aid of a multiplexer (6) and a corresponding controller (9) or by means of a multifrequency excitation scheme (FIG. 7, FIG. 8) with a plurality of sine-wave generators (5a, 5b, 5c and 5d).

FIG. 2, FIG. 5, FIG. 6, FIG. 7, FIG. 8 diagrammatically show grid sensor arrangements with 4×4 electrodes and a circular geometry. It goes without saying that the grid sensors may also be constructed in other geometries, for example rectangular cross sections. Furthermore, the number of electrodes is arbitrary in theory.

Figure 2:
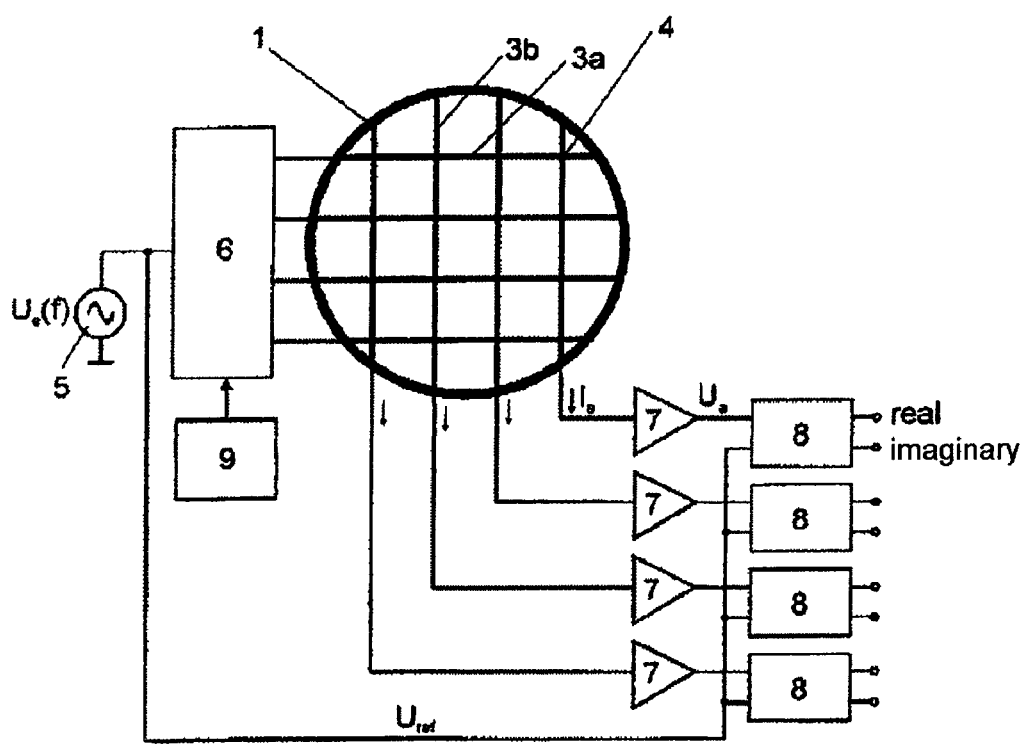

FIG. 1 and FIG. 2 diagrammatically show a grid sensor (1) having two electrode levels and associated measurement electronics (2). The grid sensor has four metal wires for each level (3a, 3b) which are stretched over the sensor cross section such that they are electrically insulated from one another. The wires are anchored in the sensor frame in such a manner that each electrode is completely electrically insulated from the other electrodes and from the frame itself. On the excitation side, the measurement electronics comprise a sine-wave generator (5), a multiplexer (6) and a controller (9). The individual transmitting electrodes (3a) on the transmitting level of the sensor are electrically connected to the outputs of the multiplexer (6). On the receiver side, each of the receiver electrodes (3b) on the receiver level is connected to a current-voltage converter (7). Vector voltmeters (8) whose reference inputs are connected to the signal output of the sine-wave generator (5) are connected to the current-voltage converters (7) in order to evaluate the complex impedance signal.

The measurement scheme of the sensor sketched in FIG. 1 is as follows:

A controller or microprocessor (9) provided for the purpose of control successively applies the sinusoidal voltage signal from the sine-wave generator (5) to the individual transmitting electrodes (3a) via the multiplexer (6). The multiplexer (6) is designed in such a manner that the sinusoidal voltage is applied only to an individual transmitting electrode (3a), whereas all other transmitting electrodes are at zero potential. At the respectively active transmitting electrode, an alternating current flows into the crossover points (4) of the wire electrodes and to the receiver electrodes (3b) which are at virtual ground. This current is proportional to the instantaneous admittance Y of the crossover point and is converted into a voltage signal $U_a$ by the current-voltage converters (7). $U_a = k \cdot I_a$, where $I_a$ denotes the alternating current at the crossover point and k denotes the transimpedance gain of the current-voltage converter. The vector voltmeters (8) compare the AC voltage signal $U_a$ with the excitation input signal $U_e$ and evaluate the magnitude and phase of said voltage signal. According to Ohm's law, the following applies to the admittance $$Y = \frac{I_a}{U_e} = \frac{U_a}{kU_e}.$$

This can be calculated directly from the resultant phase vector $U_a/U_e$.

Figure 4:
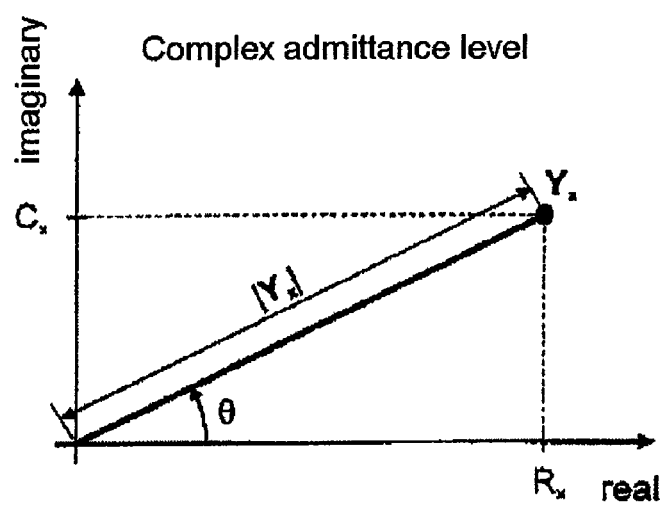

FIG. 4 illustrates the relationships of the admittance on the complex level.

Figure 3:
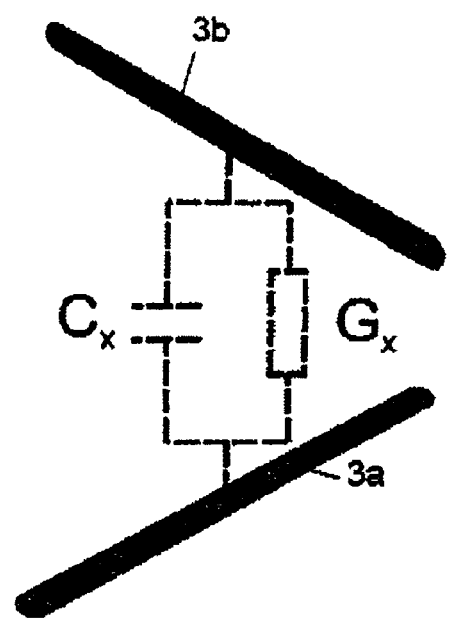

FIG. 3 illustrates the equivalent circuit diagram for a crossover point (4) and the resultant measurement variables. In this case, (3a) denotes the transmitting electrode and (3b) denotes the receiver electrode. The electrical admittance is linked to the admittance $G_x$ and the capacitance $C_x$ of the medium at the crossover point according to $$Y_x = G_x + j \cdot 2\pi f \cdot C_x$$

where $j = \sqrt{-1}$ and f is the excitation frequency of the sine-wave generator (5).

In terms of circuitry, the following variants are conceivable for implementing the vector voltmeter (8):

1. Implementation in the form of an amplitude-phase detector, the magnitude $|Y_x|$ and the phase $\theta$ of the complex output voltage ratio $U_a/U_e$ being determined. The measurement variables $G_x$ and $C_x$ can accordingly be calculated from:

$$G_x = |Y_x|\cos\theta$$
$$C_x = \frac{|Y_x|\cos\theta}{2\pi f}.$$

2. Implementation in the form of an I/Q demodulator, the real and imaginary components of the complex output voltage ratio $U_a/U_e$ being determined. The measurement variables sought then result from:

$$G_x = \text{Re}(Y_x)$$
$$C_x = \frac{\text{Im}(Y_x)}{2\pi f}.$$

3. Implementation by means of sufficiently fast temporal sampling and digital recording of the voltage signals $U_a$ and $U_e$ and their ratios with the aid of an analog/digital converter and subsequent software-based or hardware-based Fourier analysis.

In materials science and analytical chemistry, it is customary to characterize materials by their complex relative permittivity $\varepsilon_r^*$. This complex variable comprises the dielectric constant $\varepsilon_r$ and the conductivity K $$\varepsilon_r^* = \varepsilon_r - j\frac{\kappa}{2\pi f \cdot \varepsilon_0}.$$

The complex admittance is directly proportional to the complex relative permittivity $$Y = \varepsilon_r^* \cdot \varepsilon_0 * j2\pi f \cdot k_g,$$

where $k_g$ denotes a geometry factor of the measuring arrangement and $\varepsilon_0$ denotes the dielectric constant of a vacuum (8.85 pF/m).

The present arrangement is also able to determine the complex relative permittivity $\varepsilon_r^*$. A person skilled in the art is familiar with the fact that calibration with a known medium, for instance water or air, is required for this. The geometry factor $k_g$ is determined from this calibration. Consequently, the complex relative permittivity $\varepsilon_r^*$ can be determined from the admittance measurement. However, if the objective is only to distinguish substances, there is no need for calibration since the measured parameters $G_x$ and $C_x$ already have the information sought and can be directly evaluated.

Figure 5:
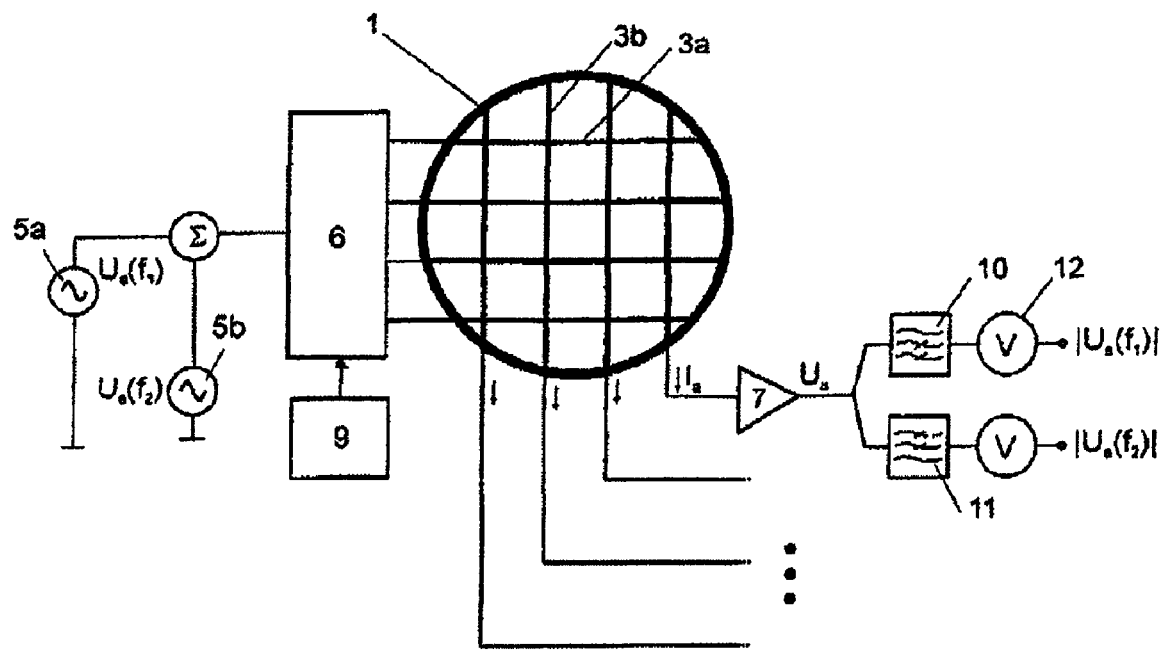

FIG. 5 shows a further circuitry variant for determining the two measurement variables $G_x$ and $C_x$. Instead of applying an AC voltage at an individual frequency f to the transmitting electrodes (3a), an AC voltage signal with two frequencies $f_1$ and $f_2$ is generated using two sine-wave generators (5a, 5b) or a dual-frequency sine-wave generator and is applied to the transmitting electrode (3a) selected by the multiplexer (6). The two frequency components are separated at the output of the current-voltage converter (7) by means of a combination of a high-pass filter (10) and a low-pass filter (11) and are evaluated individually using scalar voltmeters (12). The measurement variables $G_x$ and $C_x$ can then be determined by solving the following system of equations $$|Y_x(f_1)|^2 = G_x^2 + (j \cdot 2\pi f_1 \cdot C_x)^2$$

$$|Y_x(f_2)|^2 = G_x^2 + (j \cdot 2\pi f_2 \cdot C_x)^2.$$

The following thus apply $$C_x = \sqrt{\frac{|Y_x(f_1)|^2 - |Y_x(f_2)|^2}{(2\pi f_1)^2 - (2\pi f_2)^2}}$$

and $$G_x = \sqrt{\frac{|Y_x(f_2)|^2 \cdot (2\pi f_1)^2 - |Y_x(f_1)|^2 \cdot (2\pi f_2)^2}{(2\pi f_1)^2 - (2\pi f_2)^2}}.$$

Figure 6:
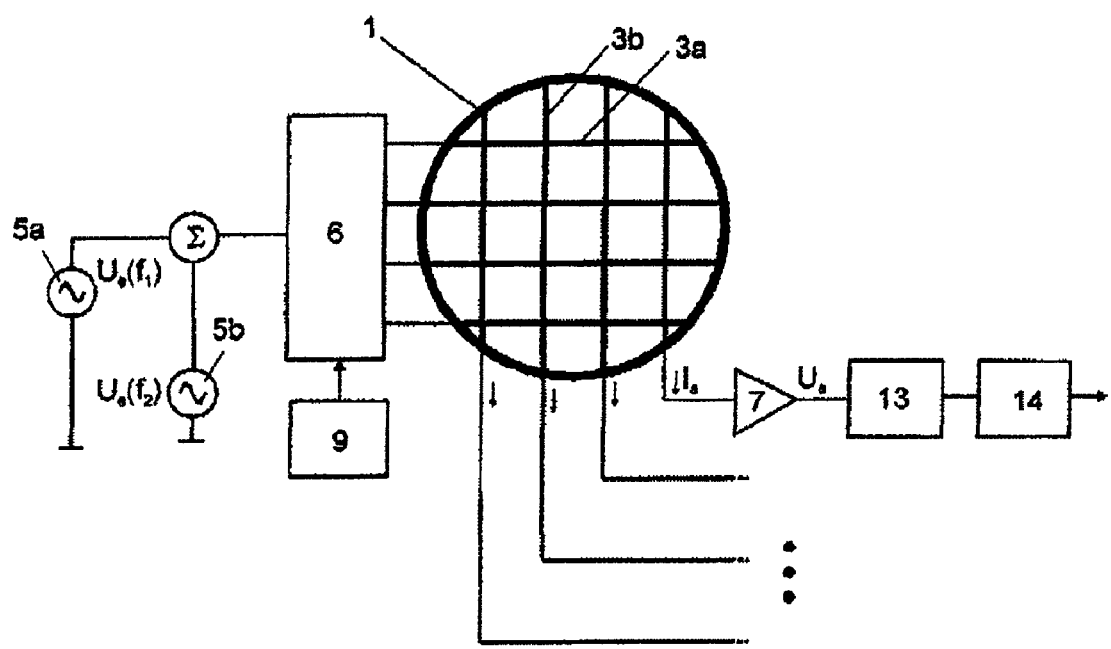

In this case, measurement of the amplitudes of the AC voltage signals by means of peak value or effective value detection, for example, is therefore sufficient. Furthermore, the magnitudes of the individual frequency components can be determined by means of analog/digital conversion (13) of the dual-frequency signal and subsequent Fourier analysis (14) (FIG. 6).

Figure 7:
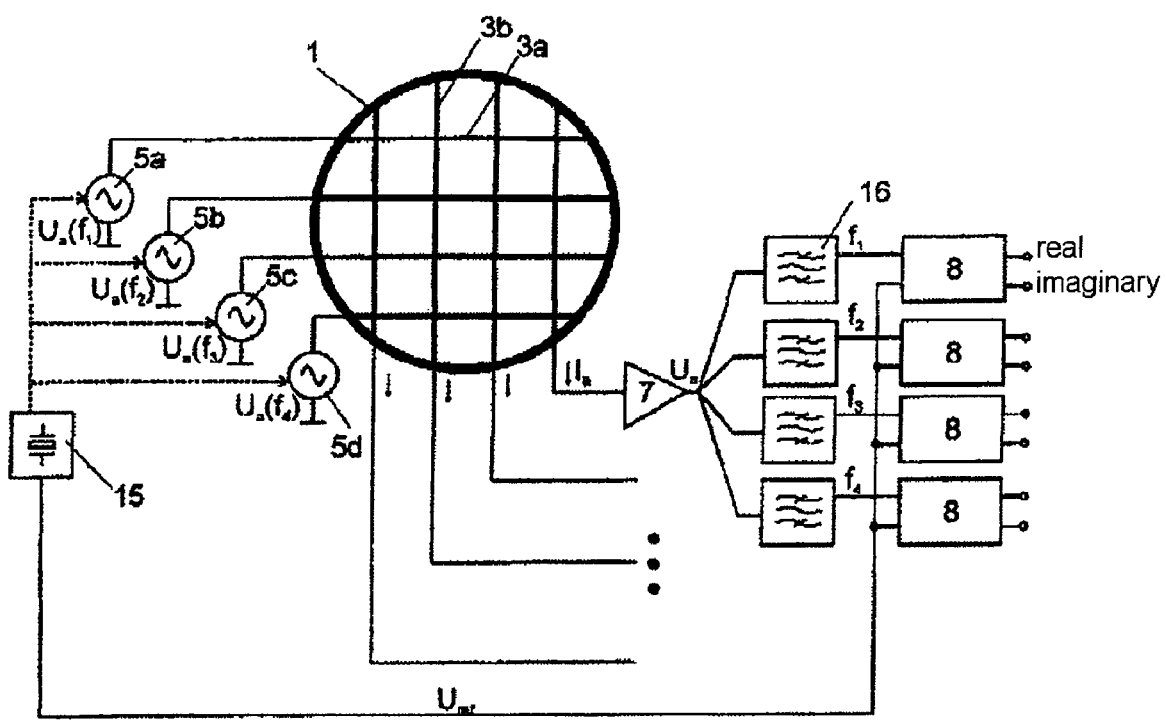
Figure 8:
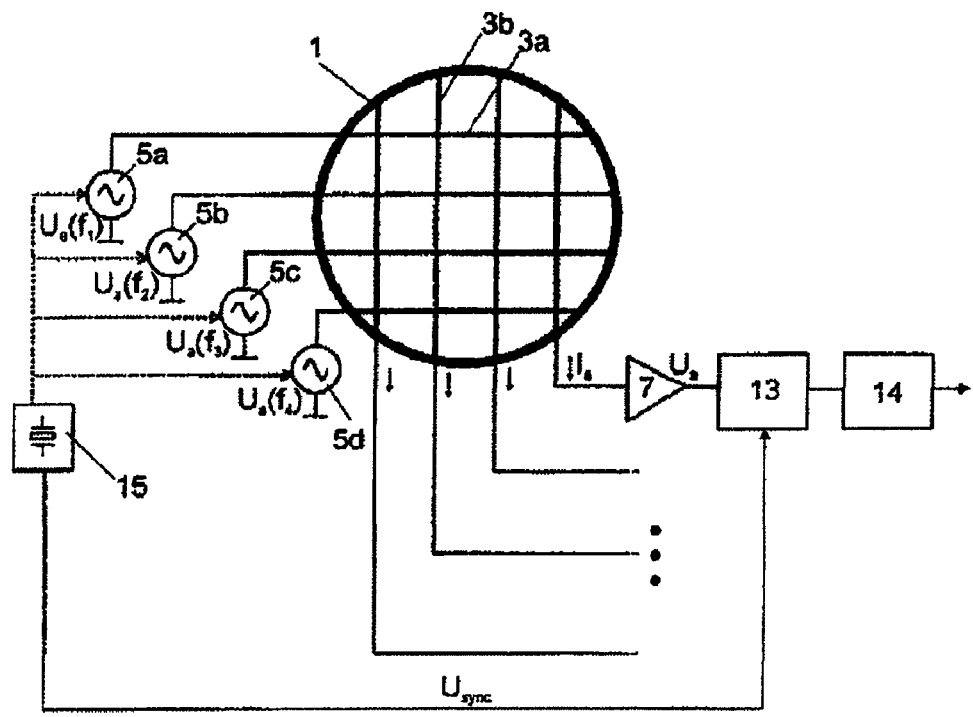

Finally, a multifrequency excitation scheme is used in the arrangement illustrated in FIG. 7 and FIG. 8. In this case, each individual transmitting electrode (3a) on the excitation level is directly connected to a sine-wave generator (5a, 5b, 5c and 5d). The sine-wave generators generate AC voltages at different frequencies but are synchronized with one another by means of a common clock generator (15). The measurement current $I_a$ is now cumulatively composed of the frequency components at the different excitation frequencies $f_1$, $f_2$, $f_3$ and $f_4$, which frequency components are weighted by the complex admittance of the crossover points. Each of these frequency components is uniquely assigned to a crossover point (4). In order to separate the signal components, bandpass filters (16) which selectively pass the respective frequency component are connected to the outputs of the current-voltage converters. In this exemplary embodiment, four bandpass filters (16) and four vector voltmeters (8) are required for each receiver wire in order to evaluate the complex output voltage signal. In this case, each of the above-mentioned implementation variants of the vector voltmeter can again be used. A bandpass filter is not required for the variant 3 (temporal sampling with subsequent Fourier analysis) illustrated in FIG. 8 since the frequency components are automatically separated in Fourier analysis (14). In this case, the sampling of the signals by means of analog/digital converters (13) must be carried out in synchronism with the clock generator (15) of the excitation signal.

For the case of a pure conductivity or capacitance measurement, the vector voltmeter (8) can be replaced with a conventional scalar voltmeter (peak value or effective value detector) since only the magnitude of the measurement signal and no longer the phase angle needs to be evaluated in this case. A pure capacitance measurement may be advantageous since the electrodes do not need to be directly electrically exposed to the medium to be investigated. This makes it possible to protect the electrodes from corrosion or electrochemical decomposition to a sufficient extent. Furthermore, the electrical insulation of the electrodes at the fixing points in the sensor frame is facilitated.

LIST OF REFERENCE SYMBOLS

1—Grid sensor
2—Measurement electronics
3a—Transmitting electrode
3b—Receiver electrode
4—Crossover point
5—Sine-wave generator
6—Multiplexer
7—Current-voltage converter
8—Vector voltmeter
9—Controller
10—High-pass filter
11—Low-pass filter
12—Scalar voltmeter
13—Analog/digital converter
14—Fourier analysis
15—Clock generator
16—Bandpass filter

The invention claimed is:

1. An arrangement for the two-dimensional measurement of different components in the cross section of a multiphase flow, comprising
   a grid sensor (1) whose grid is constructed from transmitting electrodes (3a) and receiver electrodes (3b) which are in the form of wires or rods and are arranged on two coplanar levels at a distance of a few millimeters, the electrodes within each level being arranged parallel to one another and electrodes on different levels being arranged at an angle of approximately 90° with respect to one another,
   associated measurement electronics (2) comprising at least one sine-wave generator (5) for generating an AC voltage signal as well as current-voltage converters (7) and vector voltmeters (8) for measuring the complex voltage ratio $U_a/U_e$ of the current-voltage converter output voltage and AC voltage signal, characterized in that
   at least one sine-wave generator (5) which applies an AC voltage to the transmitting electrodes (3a) is connected upstream of the transmitting electrodes (3a) on an excitation level,
   current-voltage converters (7) which amplify the alternating current flowing through the multiphase flow from at least one excitation electrode (3a) to the receiver electrodes (3b) and convert it into a voltage signal are connected downstream of the receiver electrodes (3b),
   filter groups (10, 11, 16) and vector voltmeters (8) which are used to metrologically detect the complex signal ratio $U_a/U_e$ are connected downstream of the current-voltage converter (7).

2. The arrangement as claimed in claim 1, characterized in that a multiplexer (6) which successively applies the AC voltage signal from the sine-wave generator (5) to the transmitting electrodes in a defined time regime is connected upstream of the transmitting electrodes (3a) on the excitation level.

3. The arrangement as claimed in claim 1, characterized in that an AC voltage signal with two frequency components is applied to the transmitting electrodes (3a) on the excitation level by at least one dual-frequency sine-wave generator (5a, 5b), and high-pass filters (10) and low-pass filters (11) which are matched to the two frequencies and at the outputs of which the AC voltage signals at the two carrier frequencies are analyzed by scalar voltmeters (12) are arranged downstream of each of the current-voltage converters (7).

4. The arrangement as claimed in claim 1, characterized in that an AC voltage signal with its own frequency can be applied to each of the transmitting electrodes (3a) on the excitation level by a separate sine-wave generator (5a, 5b, 5c, . . .), the sine-wave generators are connected in phase, and a set of bandpass filters (16) and vector voltmeters (8), which are used to analyze the AC voltage signals for all carrier frequencies, is connected downstream of each of the current-voltage converters (7).

5. The arrangement as claimed in claim 1, characterized in that, instead of electronic vector voltmeters (8), fast analog/digital converters (13) are arranged and can be used to electronically detect the AC voltage signals at the required sampling rate and to supply them to digital software-based or hardware-based Fourier analysis (14).

6. The arrangement as claimed in claim 1, characterized in that the electrodes of the grid sensor (1) are completely surrounded by an electrically insulating protective layer.

* * * * *